United States Patent
Ramdani

(10) Patent No.: US 7,741,504 B2
(45) Date of Patent: *Jun. 22, 2010

(54) METHOD FOR PREPARING AN ω-HALOALKYL DIALKYLHALOSILANE

(75) Inventor: Kamel Ramdani, Tupin Et Semons (FR)

(73) Assignee: Rhodia Chimie, Aubervilliers (FR)

(*) Notice: Subject to any disclaimer, the term of this patent is extended or adjusted under 35 U.S.C. 154(b) by 0 days.

This patent is subject to a terminal disclaimer.

(21) Appl. No.: 11/629,593

(22) PCT Filed: Jun. 14, 2005

(86) PCT No.: PCT/FR2005/001469

§ 371 (c)(1),
(2), (4) Date: Dec. 28, 2007

(87) PCT Pub. No.: WO2006/003323

PCT Pub. Date: Jan. 12, 2006

(65) Prior Publication Data

US 2008/0287700 A1    Nov. 20, 2008

(30) Foreign Application Priority Data

Jun. 16, 2004    (FR) ................... 04 06502

(51) Int. Cl.
*C07F 7/04*    (2006.01)
(52) U.S. Cl. ................ 556/473; 556/466; 556/479
(58) Field of Classification Search ........... None
See application file for complete search history.

(56) References Cited

U.S. PATENT DOCUMENTS 6,388,119 B1 * 5/2002 Bauer et al. ............ 556/479

7,307,180 B2 * 12/2007 Guennouni et al. ......... 556/473

FOREIGN PATENT DOCUMENTS

| EP | 1156052 B1 | 11/2001 |
| FR | 2843392 A1 | 2/2004 |
| WO | WO 03/048169 A1 * | 6/2003 |

OTHER PUBLICATIONS

Aoki et al., {Immobilization of chiral phosphine ligands on silica gel by means of the allylsilane method and their use for catalytic asymmetric reactions, Tetrahedron: Asymmetry (2004), 15(11), 1771-1777}.*

* cited by examiner

*Primary Examiner*—Jafar Parsa
*Assistant Examiner*—Chukwuma O Nwaonicha
(74) *Attorney, Agent, or Firm*—Buchanan Ingersoll & Rooney PC

(57) ABSTRACT

The present invention relates to a method for preparing an omega-haloalkyl dialkylhalosilane by means of a hydrosilylation reaction in the presence of a catalytically effective amount of a hydrosilylation catalyst containing a platinum group metal. The catalytic metal is recovered by (i) subjecting the distillation residue to controlled hydrolysis to release the gaseous H-Hal haloacid, and providing an aqueous medium containing the catalytic metal with a low hydrolysable halide content Si-Hal=2%, expressed by weight of Hal, then (2i) recovering the platinum group catalytic metal from said aqueous medium by means of one of the conventional techniques specific to catalyst manufacturers that do not use a solid adsorbent and operate in ordinary facilities that do not have to be acid-resistant.

9 Claims, No Drawings

METHOD FOR PREPARING AN ω-HALOALKYL DIALKYLHALOSILANE

This application is an application under 35 U.S.C. Section 371 of International Application Number PCT/FR2005/001469 filed on Jun. 14, 2005.

The present invention relates to a method for preparing an ω-haloalkyl dialkylhalosilane.

The present invention notably relates to a method for preparing 3-chloropropyl dimethylchlorosilane, by hydrosilylation of dimethyl hydrochlorosilane by means of allyl chloride and a catalyst based on a platinum metal and recovery of said metal.

In this type of reaction, the amounts of platinum metal employed are often high in order to obtain a satisfactory yield. This amount of metallic catalyst is generally greater than 30 ppm, calculated relative to the total weight of the reaction mixture. For the process to remain economically viable, it is desirable to be able to recover the platinum metal for reuse as catalyst.

A method for preparing an ω-haloalkyl dialkylhalosilane of formula (I) was proposed in WO-A-2004/016628:

$$\text{Hal-}(R^2R^3)\text{Si}—(CH_2)_s\text{-Hal}$$

by a reaction of hydrosilylation of a reaction mixture comprising a silane of formula (II):

$$\text{Hal-}(R^2R^3)\text{Si}—H$$

and an alkene halide of formula (III):

$$CH{=\!=}CH—(CH_2)_{s-2}\text{Hal}$$

in the presence of a catalytically effective amount of a hydrosilylation catalyst based on a platinum metal.

In the above formulae:
- the symbol Hal represents a halogen atom selected from the atoms of chlorine, bromine and iodine, the chlorine atom being preferred,
- the symbols $R^2$ and $R^3$, which may be identical or different, each represent a monovalent hydrocarbon group selected from a linear or branched alkyl radical having from 1 to 6 carbon atoms and a phenyl radical, and
- s represents an integer between 2 and 10 inclusive.

In said process, at the end of the hydrosilylation reaction, the reaction mixture is distilled in order to separate the product of formula (I) from it, this distillation leading to a liquid residue comprising a little of the product formed of formula (I) that was not separated by distillation, by-products and the catalytic metal employed.

According to the teaching of the prior art, the catalytic metal can be recovered from the liquid distillation residue by carrying out the following stages:
- bringing the liquid residue into direct contact with an effective amount of a solid that adsorbs the catalytic metal; or alternatively bringing the liquid residue into contact with water in order to hydrolyze it, thus obtaining an aqueous phase and an organic phase, then treatment of the organic phase or the combined aqueous phase/organic phase with an effective amount of a solid that adsorbs the catalytic metal; and
- separation of the adsorbent from the metal in order to recover said metal.

Bringing the distillation residue into contact with water renders this residue inert by converting all or at least most of the Si—Hal functions to Si—OH functions and siloxane chains Si—O—Si according to the chemical reactions:

$$\text{Si-Hal} + H_2O \rightarrow \text{Si—OH} + \text{H-Hal}$$

$$\text{Si—OH} + \text{Si-Hal} \rightarrow \text{Si—O—Si} + \text{H-Hal and Si—OH} + \text{Si—OH} \rightarrow \text{Si—O—Si} + H_2O$$

The method just described is not one of the most economical and moreover it has the drawback of being toxic to the environment owing to the need for handling a residue containing, after hydrolysis, an aqueous phase having a high acidity (H-Hal), for example in the range by weight from 40 to 50%.

In this context, one of the essential aims of the present invention is to propose a method for preparing an ω-haloalkyl dialkylhalosilane of the type described previously in which the reaction kinetics of hydrolysis is perfectly under control so as to be able to minimize the amount of H-Hal formed, which is present in the aqueous phase of hydrolysis.

Another essential aim of the present invention is to propose a method for preparing an ω-haloalkyl dialkylhalosilane in which the procedure employed in the recovery of the catalytic metal is simplified in that it no longer makes use of a stage of adsorption of the catalytic metal on an adsorbent solid.

Another essential aim of the present invention is to propose a method for preparing an ω-haloalkyl dialkylhalosilane that can result in a residue that is easy to handle and has a low content of hydrolyzable halide Si-Hal≦2%, expressed as weight of Hal.

Yet another aim of the present invention is to supply a method for preparing an ω-haloalkyl dialkylhalosilane in which the catalytic metal is recovered from the distillation residue by applying conventional techniques familiar to catalyst manufacturers, but now without employing any adsorbent solid and meeting all the requirements of industrial feasibility, notably the absence of hazardousness as the acidity is extremely limited and the possibility of operation without the need to use expensive acid-resistant materials.

These aims, among others, are achieved by the present invention, which therefore relates to a method for preparing an ω-haloalkyl dialkylhalosilane of formula (I):

$$\text{Hal-}(R^2R^3)\text{Si}—(CH_2)_s\text{-Hal}$$

by a reaction of hydrosilylation of a reaction mixture comprising a silane of formula (II):

$$\text{Hal-}(R^2R^3)\text{Si}—H$$

and an alkene halide of formula (III):

$$CH{=\!=}CH—(CH_2)_{s-2}\text{Hal}$$

in the presence of a catalytically effective amount of a hydrosilylation catalyst based on a platinum metal.

In the above formulae:
- the symbol Hal represents a halogen atom selected from the atoms of chlorine, bromine and iodine, the chlorine atom being preferred,
- the symbols $R^2$ and $R^3$, which may be identical or different, each represent a monovalent hydrocarbon group selected from a linear or branched alkyl radical having from 1 to 6 carbon atoms and a phenyl radical, and
- s represents an integer between 2 and 10 inclusive.

In said process, at the end of the hydrosilylation reaction, the reaction mixture is distilled in order to separate the product of formula (I) from it, this distillation leading to a liquid residue comprising a little of the product formed of formula (I) that was not separated by distillation, by-products and the catalytic metal employed, then an operation of recovery of the catalytic metal from said residue, said method being characterized in that, in order to recover the catalytic metal, the following are carried out:

controlled hydrolysis of the residue resulting from distillation of the reaction mixture containing the catalytic platinum metal, said metal being in its original form as catalyst or in a converted form, this controlled hydrolysis being employed according to a particular procedure that permits:

a) reaction, with water, of the Si-Hal functions of the product of formula (I) present in the residue, b) release of the halogen-containing acid H-Hal formed essentially in the gaseous state, and c) the provision of an aqueous medium containing the catalytic metal, which has a low content of hydrolyzable halide Si-Hal≦2%, expressed by weight of Hal;

then recovery, from said aqueous medium, of the catalytic platinum metal by application of one or other of the conventional techniques familiar to catalyst manufacturers without the need to use any adsorbent solid and working in an ordinary apparatus that does not need to be acid-resistant.

The platinum metal is selected from platinum, iridium, palladium, rhodium, ruthenium and osmium, the preferred metal being iridium. Within the scope of this preferred embodiment, Ir-based catalysts that are suitable are in particular:

[IrCl(CO)(PPh$_3$)$_2$]
[Ir(CO)H(PPh$_3$)$_3$]
[Ir(C$_8$H$_{12}$)(C$_5$H$_5$N)P(C$_6$H$_{11}$)$_3$]PF$_6$
[IrCl$_3$].nH$_2$O
H$_2$[IrCl$_6$].nH$_2$O
(NH$_4$)$_2$IrCl$_6$
Na$_2$IrCl$_6$
K$_2$IrCl$_6$
KIr(NO)Cl$_5$
[Ir(C$_8$H$_{12}$)$_2$]$^+$BF$_4^-$
[IrCl(CO)$_3$]$_n$
H$_2$IrCl$_6$
Ir$_4$(CO)$_{12}$
Ir(CO)$_2$(CH$_3$COCHCOCH$_3$)
Ir(CH$_3$COCHCOCH$_3$)
IrBr$_3$
IrCl$_3$
IrCl$_4$
IrO$_2$
(C$_6$H$_7$)(C$_8$H$_{12}$) Ir.

Within the scope of the even more preferred embodiment mentioned previously, other Ir-based catalysts that are even more suitable are selected from the group of iridium complexes of formula:

$$[Ir(R^4)Hal]_2 \qquad (IV)$$

in which:
the symbol $R^4$ represents an unsaturated hydrocarbon ligand comprising at least one carbon=carbon double bond and/or at least one C≡C triple bond, it being possible for these unsaturated bonds to be conjugated or unconjugated, said ligand: being linear or cyclic (mono- or polycyclic), having from 4 to 30 carbon atoms, having from 1 to 8 ethylenic and/or acetylenic unsaturations and optionally comprising one or more heteroatoms such as an oxygen atom and/or a silicon atom;
the symbol Hal is as defined above.

As examples of iridium complexes of formula (IV) that are even more suitable, we may mention those in whose formula:
the symbol $R^4$ is selected from 1,3-butadiene, 1,3-hexadiene, 1,3-cyclohexadiene, 1,3-cyclooctadiene, 1,5-cyclooctadiene, 1,5,9-cyclododecatriene and norbornadiene, and the following compounds of formula:

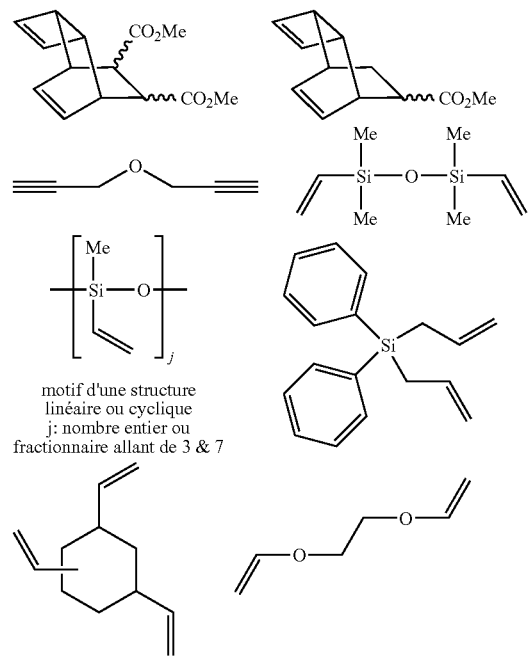

motif d'une structure linéaire ou cyclique
j: nombre entier ou fractionnaire allant de 3 & 7 unit of linear or cyclic structure j: integer or fractional number from 3 to 7 the symbol Hal represents a chlorine atom.

As specific examples of iridium complexes that are even more suitable, we may mention the following catalysts:
di-μ-chlorobis(divinyltetramethyldisiloxane)-diiridium,
di-μ-chlorobis(η-1,5-hexadiene)diiridium,
di-μ-bromobis(η-1,5-hexadiene)diiridium,
di-μ-iodobis(η-1,5-hexadiene)diiridium,
di-μ-chlorobis(η-1,5-cyclooctadiene)diiridium,
di-μ-bromobis(η-1,5-cyclooctadiene)diiridium,
di-μ-iodobis(η-1,5-cyclooctadiene)diiridium,
di-μ-chlorobis(η-2,5-norbornadiene)diiridium,
di-μ-bromobis(η-2,5-norbornadiene)diiridium,
di-μ-iodobis(η-2,5-norbornadiene)diiridium.

While remaining within the scope of the present invention, it is possible to use, besides the catalyst based on a platinum metal, at least one hydrosilylation reaction promoter.

The following may be mentioned as optional promoter or promoters: a compound, which can for example be in the form of a ligand or an ionic compound, selected in particular from the group comprising: an organic peroxide; a carboxylic acid; a salt of a carboxylic acid; a tertiary phosphine; a phosphite, for example an optionally mixed alkyl and/or aryl phosphite; an amine, an amide; a linear or cyclic ketone; a linear or cyclic ketone; a trialkylhydrosilane; benzothriazole; phenothiazine; a compound of the type: trivalent metal-(C$_6$H$_5$)$_3$ where metal=As, Sb or P; a mixture of amine or of cyclohexanone with an organosilicon compound containing one or more ≡Si—H groups; the compounds CH$_2$=CH—CH$_2$—OH or CH$_2$=CH—CH$_2$—OCOCH$_3$; a lactone; a mixture of cyclohexanone and triphenylphosphine; an ionic compound, for example a nitrate or a borate of an alkali metal or of imidazolinium, a phosphonium halide, a quaternary ammonium halide, or a tin(II) halide.

The optional promoter or promoters, when one (or more) is/are used, is/are generally introduced at the start of reaction, either in their normal state, or as a premix based on: promoter(s)+catalyst(s); or promoter(s)+all or part of the diorganohalosilane of formula (II); or promoter(s)+all or part of the alkene halide of formula (III).

In another preferred embodiment, the catalyst can be used in a homogeneous liquid medium, as described in JP-B-2.938.731 and EP-A-1 156 052. In this context, the reaction can be carried out either continuously, or semi-continuously, or discontinuously. At the end of the operation, the product formed of formula (I) and the catalytic platinum metal are recovered, as mentioned above.

The amount of alkene halide of formula (III) used is preferably from 1 to 2 mol per 1 mol of silane of formula (II). As for the amount of catalyst(s) (i), expressed as weight of platinum metal, it is in the range from 1 to 10 000 ppm, preferably from 10 to 2000 ppm and more preferably from 20 to 1000 ppm based on the weight of silane of formula (II).

According to the present invention, the liquid distillation residue is therefore brought into contact with a sufficient amount of water to transform all or at least most of the Si-Hal functions to silanol functions Si—OH and siloxane chains Si—O—Si.

Disregarding the teachings of the present invention, bringing the liquid residue into contact with water certainly leads to hydrolysis of hydrolyzable Si-Hal functions, but the halogen-containing acid H-Hal thus formed then dissolves in the medium. A person skilled in the art will be familiar with simple means for breaking down this halogen-containing acid, for example by chemical reaction with a base (for example NaOH); the experiments that we have conducted show, however, that in the presence of water, acidity and a base, the residue resulting from distillation of the reaction mixture then leads to the formation of a sludge which is difficult to handle.

The distillation residue generally contains a certain proportion of halosilane of formula (I) that is not separated by distillation and the corresponding disilane, which leads to total halogen contents of the order of 40 to 50 wt. % and of ionic halogen of the order of 15 to 25 wt. %. Total halogen means all of the halogen atoms present in the residue; ionic halogen means all of the so-called hydrolyzable halogens, i.e. essentially the Si-Hal functions that can react with water to form the corresponding halogen-containing acid.

It is recommended to carry out hydrolysis in semi-continuous mode by pouring water onto the residue; this hydrolysis is "controlled" by adjusting the rate of introduction of the water to avoid any accumulation of water in the medium so that the H-Hal acid formed at each moment is not dissolved in the aqueous phase; in fact, the halogen-containing acid H-Hal is very soluble in water and to promote its removal in gaseous form, the water flow rate needs to be adjusted so that there is practically a water deficit, relative to stoichiometry corresponding to dissolution of the acid, throughout the reaction.

The amount of water used is closely related on the one hand to the degassing capacity of the halogen-containing acid, which is a function of the water accumulated in the medium over time, and on the other hand to the operating parameters, for example the stirring speed of the hydrolysis reactor, the temperature and/or the presence or absence of an inert gas performing the role of carrier of the halogen-containing acid ("stripping" system). Advantageously, degassing of the halogen-containing acid formed is promoted by stripping using a gas that is inert with respect to the hydrogen halide H-Hal formed and the products making up the residue; in this case, it is recommended to use nitrogen or argon and avoid steam or alcohol, which react with the halosilanes.

Controlled hydrolysis can be carried out at atmospheric pressure or at reduced pressure and, optionally, in the presence of an inert gas as explained above.

In practice, the amount of water used is in the range from 1 to 5 mol, and preferably from 1 to 3 mol, per 1 mol of hydrolyzable halogen (Si-Hal function).

Also in practice, the water is added to the distillation residue at a controlled flow rate so as to avoid any accumulation of water in the medium and thus dissolution of the H-Hal acid formed at each moment. The precise value of this flow rate will depend on the geometric characteristics of the hydrolysis reactor and on the stripping conditions (type of inert gas, flow rate of the inert gas, hydrolysis temperature, speed of reactor stirring) in the case when this operating system is used. A person skilled in the art will easily be able to determine, using simple tests, the precise value of the flow rate to be employed for each operation.

As an illustrative but non-limiting example, in the case when working in a reactor of 1 to 3 liters, containing at least 400 g of materials, equipped with a mechanical stirrer operating at a speed from 200 to 600 rev/min, with inert gas scavenging at a flow rate from 10 to 50 g of gas per hour and heated at a temperature in the range from 40 to 60° C., the water is added to the distillation residue at a flow rate in the range from 0.001 to 0.04 mol of water, and preferably from 0.002 to 0.015 mol of water per minute and per mole of hydrolyzable halogen.

In the case when hydrolysis is carried out on the distillation residue without control, the halogen-containing acid formed is then dissolved partially or completely in the medium and therefore a proportion of ionic halogen above 15 wt. % is maintained. Carried out in this way, the process leads to the formation of an aqueous phase and an organic phase with equal-mass distribution of the metal catalyst between these two phases; this route does indeed make it possible to achieve the objective of rendering the reactive residue inert, but in time it leads to the formation of a sludge that is difficult to handle, incompatible with a reliable and reproducible process; moreover, this route presents the problem of qualitative and quantitative analyses of the metal catalyst.

Controlled hydrolysis can be carried out at temperatures from 0° C. to 100° C. at atmospheric pressure. As the reaction is exothermic, it is preferable to add the water at moderate temperatures in the range from 10 to 80° C. Temperature control may prove necessary. On completion of adding the water to the residue, the mixture obtained is single-phase, comprising an organic phase containing the catalytic metal to be recovered.

Preferably, the product of formula (I) is 3-chloropropyl dimethylchlorosilane, the product of formula (II) is dimethyl hydrochlorosilane and the product of formula (III) is allyl chloride. In this case, the hydrogen halide formed H-Hal is HCl.

The following examples illustrate the invention without limiting its scope.

In the examples given below, first a reaction of hydrosilylation of dimethyl hydrochlorosilane on the allyl chloride is carried out in the presence of 500 ppm of di-µ-chlorobis(η-1,5-cyclooctadiene)diiridium relative to the weight of dimethyl hydrochlorosilane, in a reactor equipped with a stirrer, a reflux condenser and a thermometer. The dimethyl hydrochlorosilane is added dropwise to the reaction mixture for 7 hours at a temperature of 38° C. The final medium thus obtained constitutes the reaction mixture that is treated in some of the following examples. The 3-chloropropyl dimethylchlorosilane is separated from the reaction mixture by distillation, giving a liquid distillation residue containing the catalyst; it is this distillation residue that is treated in the following examples.

EXAMPLE 1

Controlled Hydrolysis of the Residue to Get Below the Limiting Content of 2 wt. % of Ionic Chlorine Feed 400 g of distillation residue containing 1.2 wt. % of iridium into a 1-liter reactor equipped with a mechanical stirrer (stirrer of the three-blade type operating at 400 rev/min) and with argon scavenging (flow rate 14 g/h). The content of hydrolyzable chlorine is 20 wt. %, corresponding to 2.25 mol. The reaction mixture is stirred, and heated at 50° C.

Add 120 g of water at a flow rate of 0.400 g/min, i.e. 0.009 mol of water per minute and per mole of hydrolyzable chlorine.

Maintain the temperature conditions throughout the test. The hydrochloric acid released in the form of gas is trapped in a column in which a stream of soda diluted to 30 wt. % in water circulates. Recover the final medium and analyze for ionic chlorine: the final content is 0.13 wt. %.

For this experiment, the molar ratio of water to hydrolyzable chlorine is 2.96.

EXAMPLE 2

Controlled Hydrolysis of the Residue to Get Below the Limiting Content of 2 wt. % of Ionic Chlorine Feed 800 g of distillation residue identical to that used in Example 1 and containing 1.2 wt. % of iridium, into a 1-liter reactor equipped with a mechanical stirrer (stirrer of the three-blade type operating at 400 rev/min) and with argon scavenging (flow rate 14 g/h). The reaction mixture is stirred, and heated at 50° C. The content of hydrolyzable chlorine is 4.5 mol.

Then add 160 g of water at a flow rate of 0.5 g/min, i.e. 0.006 mol of water per minute and per mole of hydrolyzable chlorine, and maintain the temperature conditions for 1 hour. Recover the final medium and analyze for ionic chlorine: the final content is 0.30 wt. %.

For this experiment, the molar ratio of water to hydrolyzable chlorine is 1.97.

COMPARATIVE EXAMPLE

Hydrolysis of the Residue without being Able to Get Below the Limiting Content of 2 wt. % of Ionic Chlorine Feed 800 g of distillation residue identical to that used in Example 1 and containing 1.2 wt. % of iridium, into a 1-liter reactor equipped with a mechanical stirrer (stirrer of the three-blade type operating at 400 rev/min) and with argon scavenging (flow rate 14 g/h). The reaction mixture is stirred, and heated at 50° C. The content of hydrolyzable chlorine is 4.5 mol.

Then add 160 g of water at a flow rate of 5 g/min, i.e. 0.06 mol of water per minute and per mole of hydrolyzable chlorine. Maintain the temperature conditions for 1 hour. Recover the final medium and analyze for ionic chlorine: the final content is 4.30 wt. %.

For this experiment, the molar ratio of water to hydrolyzable chlorine is 1.97.

The invention claimed is:

1. A method for preparing an ω-haloalkyl dialkylhalosilane of formula (I):

$$\text{Hal-}(R^2R^3)\text{Si}-(CH_2)_s\text{-Hal} \qquad (I)$$

by reacting a silane of formula (II):

$$\text{Hal-}(R^2R^3)\text{Si}-H \qquad (II)$$

with an alkene halide of formula (III):

$$CH{=}CH-(CH_2)_{s-2}\text{Hal} \qquad (III)$$

in the presence of a catalytically effective amount of a platinum metal hydrosilylation catalyst, wherein said platinum metal is selected from the group consisting of platinum, iridium, palladium, rhodium, ruthenium and osmium,
wherein, in the above formulas:
the symbol Hal represents a halogen atom selected from the group consisting of chlorine, bromine and iodine,
the symbols $R^2$ and $R^3$, which may be identical or different, each represent a monovalent hydrocarbon group selected from a linear or branched alkyl radical having from 1 to 6 carbon atoms and a phenyl radical, and
represents an integer between 2 and 10, inclusive,
said process comprising distilling the reaction mixture at the end of the hydrosilylation reaction and separating the product of formula (I) from the reaction mixture, wherein said distillation forms a liquid residue comprising the product of formula (I) that was not separated by distillation, by-products and the platinum metal catalyst, said process further comprising recovering the catalytic metal from said residue, wherein said method of recovering the catalytic metal from said residue comprises:
1) performing the controlled hydrolysis of the residue resulting from distillation of the reaction mixture containing the catalytic platinum metal by the addition of water wherein the rate of introduction of the water is controlled to avoid any accumulation of water in the medium so that the H-Hal acid formed at each moment is not dissolved in the aqueous phase, said metal being in its original form as catalyst or in a converted form, wherein said controlled hydrolysis:
   a) reacts the Si-Hal functions of the product of formula (I) present in the residue with water,
   b) releases the halogen-containing acid, H-Hal, formed in the hydrolysis essentially in the gaseous state, and
   c) the aqueous medium present after the completion of the addition of water containing the catalytic metal has a content of hydrolyzable halide Si-Hal≦2%, expressed by weight of Hal; and,
2) recovering the catalytic platinum metal without the use of any adsorbent solid and using ordinary apparatus that does not need to be acid-resistant.

2. The method as claimed in claim 1 wherein s is equal to three and the platinum metal is iridium.

3. The method as claimed in claim 2, wherein the catalyst corresponds to the formula:

$$[\text{Ir}(R^4)\text{Hal}]_2 \qquad (IV)$$

wherein:
the symbol $R^4$ represents an unsaturated hydrocarbon ligand comprising at least one carbon=carbon double bond and/or at least one C≡C triple bond, it being possible for these unsaturated bonds to be conjugated or unconjugated, said ligand: being linear or cyclic (mono- or polycyclic), having from 4 to 30 carbon atoms, having from 1 to 8 ethylenic and/or acetylenic unsaturations and optionally comprising one or more heteroatoms.

4. The method as claimed in claim 3, wherein the catalyst is selected from the group consisting of:
di-μ-chlorobis(divinyltetramethyldisiloxane)-diiridium,
di-μ-chlorobis(η-1,5-hexadiene)diiridium,
di-μ-bromobis(η-1,5-hexadiene)diiridium,
di-μ-iodobis(η-1,5-hexadiene)diiridium,
di-μ-chlorobis(η-1,5-cyclooctadiene)diiridium,
di-μ-bromobis(η-1,5-cyclooctadiene)diiridium,
di-μ-iodobis(η-1,5-cyclooctadiene)diiridium,
di-μ-chlorobis(η-2,5-norbornadiene)diiridium,
di-μ-bromobis(η-2,5-norbornadiene)diiridium, and
di-μ-iodobis(η-2,5-norbornadiene)diiridium.

5. The method as claimed in claim 3, wherein the catalyst is present in a content calculated as weight of metallic catalyst of greater than 30 ppm calculated relative to the total weight of the reaction mixture formed by the products of formula (I), (II) and (III).

6. The method as claimed in claim 1, wherein hydrolysis is carried out in semi-continuous mode.

7. The method as claimed in claim 1, wherein said release of the halogen-containing acid formed is promoted by stripping using a gas that is inert with respect to the hydrogen halide H-Hal formed and the products making up the residue.

8. The method as claimed in claim 1, wherein the amount of water used is in the range from 1 to 5 mol per 1 mol of hydrolyzable halogen.

9. The method as claimed in claim 1, wherein the compound of formula (I) is 3-chloropropyl dimethylchlorosilane, the compound of formula (II) is dimethyl hydrochlorosilane and the compound of formula (III) is allyl chloride.

* * * * *